(12) United States Patent
Paley (10) Patent No.: US 10,076,439 B2
(45) Date of Patent: Sep. 18, 2018

(54) FECAL MATTER CONTAINMENT DEVICE

(71) Applicant: Helpful Products 4U, LLC, Glendale, WI (US)

(72) Inventor: James K. Paley, Glendale, WI (US)

(73) Assignee: Helpful Products 4U, LLC, Glendale, WI (US)

(*) Notice: Subject to any disclaimer, the term of this patent is extended or adjusted under 35 U.S.C. 154(b) by 308 days.

(21) Appl. No.: 14/897,000

(22) PCT Filed: Jun. 11, 2014

(86) PCT No.: PCT/US2014/041916
§ 371 (c)(1),
(2) Date: Dec. 9, 2015

(87) PCT Pub. No.: WO2014/201121
PCT Pub. Date: Dec. 18, 2014

(65) Prior Publication Data
US 2016/0106570 A1    Apr. 21, 2016

Related U.S. Application Data

(60) Provisional application No. 61/833,968, filed on Jun. 12, 2013.

(51) Int. Cl.
*A61F 5/44* (2006.01)
*A61F 13/49* (2006.01)
(Continued)

(52) U.S. Cl.
CPC .............. *A61F 5/443* (2013.01); *A61F 5/441* (2013.01); *A61F 5/4405* (2013.01); *A61F 5/451* (2013.01); *A61F 13/49007* (2013.01)

(58) Field of Classification Search
CPC ........ A61F 5/443; A61F 5/4405; A61F 5/441; A61F 5/451; A61F 13/49007
See application file for complete search history.

(56) References Cited

U.S. PATENT DOCUMENTS

| 4,445,898 A | 5/1984 | Jensen |
| 8,277,427 B2 | 10/2012 | Edvardsen et al. |
| 2002/0198507 A1 | 12/2002 | Ferguson McCorvey |

FOREIGN PATENT DOCUMENTS

| AT | 1649 U2 | 9/1997 |
| WO | 0000128 A1 | 1/2000 |

OTHER PUBLICATIONS

Extended European Search Report dated Feb. 10, 2017. Patent Application No. 14811084.4-1664 / 3007658 / PCT/US2014041916—(8) pages.

*Primary Examiner* — Tatyana Zalukaeva
*Assistant Examiner* — Ilya Treyger
(74) *Attorney, Agent, or Firm* — Boyle Fredrickson S.C.

(57) ABSTRACT

A single use device for capturing fecal matter excreted from the anus of a user. The device includes a flexible fecal matter container having a closed end and an opening that is in fluid communication with a volume enclosed by the flexible container. An adhesive is disposed about the opening of the flexible container and has a first side that is secured to the flexible container. A second side of the adhesive is constructed to be removably applied to the epidermis of the user proximate an anal opening of the user. The adhesive is shaped to cooperate with the epidermis to circumscribe the anus in a sealed manner without interfering or overlapping anatomy associated with urinary function or medical devices, such as a catheter, associated therewith.

16 Claims, 8 Drawing Sheets

(51) Int. Cl.
*A61F 5/443* (2006.01)
*A61F 5/451* (2006.01)
*A61F 5/441* (2006.01)

FECAL MATTER CONTAINMENT DEVICE

CROSS-REFERENCE TO RELATED PATENTS

This application claims priority to U.S. Provisional Patent Application Ser. No. 61/833,968 filed on Jun. 12, 2013 titled "Fecal Matter Containment Device" and the disclosure of which is expressly incorporated herein.

FIELD OF THE INVENTION

The present invention relates to incontinence care and, more specifically, to a fecal matter containment device that maintains segregation of fecal matter from anatomy and medical devices adjacent the anus of a user.

BACKGROUND OF THE INVENTION

The progression of medical science, various environmental considerations, and healthy lifestyle choices have resulted in dramatic increases in life expectancies in many developed and even underdeveloped countries. With extended life durations, more and more people, even "healthy" adults and/or children, can be subject to intermittent or extended periods of fecal incontinence or other infirmities which render the ability to use a restroom or even a bedpan extremely difficult if not impossible. As is readily understood, exposure to fecal matter, for any duration, can be detrimental to tissue health such as maceration or ulcers, patient comfort, and general environment cleanliness and sanitation.

Commonly, persons suffering from fecal incontinence have some degree of mobility but may have a degree of mobility that inhibits expedient if any use of restroom facilities if suffering from fecal incontinence. Users with limited mobility commonly require the assistance of caregivers or the like associated with assisting with the user to restrooms or tending to the user so as to limit the exposure or duration of exposure of the user to fecal excrement. Due to the availability of such caregivers and/or the desired privacy of users with no appreciable mental infirmities, some users may attempt unassisted use of restroom facilities which could expose the user to risk of injury or exacerbate an underlying infirmity.

Various fecal matter containment appliances are commonly ill-suited for use with the area of the user proximate the anal opening. The contours of the anal cleft and the pressures associated with a prone patient position generally result in other appliances, such as ostomy appliances or the like, as being ill suited for use with cooperation of the anal cleft. Further, the lack of any ancillary structure permanently or temporality affixed to the anatomy of the user renders use of such appliance as being associated with the anus impractical if not ill advised. Commonly, the containment device cooperates with an ostometric appliance rather than the tissue of the patient so as to maintain isolation between the containment device and the tissue. Commonly, the openings associated with use of such devices directly cooperate with the stoma appliance so as to maintain the integrity and condition of the tissue surrounding the anatomic device and have generally rigid constructions so as to facilitate a secure interface therewith. Such appliances are also commonly associated with the abdominal wall to facilitate the convenience of the user with interaction with the appliance. The anatomic location as well as the contour of the anatomy surrounding the anus renders such appliances ill-suited for cooperation with the area proximate the anus. Understandably, not all fecal incontinences support the intrusive and excessive alteration of the anatomy of the user associated with ostometric appliances. Known anal fecal matter collecting appliances, sometimes referred to as fecal bags, suffer from various drawbacks.

In addition to the considerations associated with user comfort referred to above, another aspect of fecal containment appliances is associated with maintaining the integrity of the tissue surrounding the anus. Repeated removal and replacement of a fecal bag can, result in injury to the tissue or other complications associated with extended periods of placement of the fecal containment appliance. Aggressive adhesives or adhesives having a high tack adhesion parameter can damage the tissue during removal of the appliance. Improper initial placement of the adhesive can result in replacement of the adhesive during each replacement of the appliance which only exacerbates the undesirable affects associated with repeated placement and removal of the adhesive. Unfortunately, less aggressive adhesives can result in configurations wherein the containment appliance comes loose or mores relative to the anus during use of the same. Partial engagement of the engagement interface can result in leakage from the appliance and exacerbate the considerations associated with user tissue care as excrement may be held in contact with surrounding tissue for extended durations and/or may soil undergarments and/or bedding.

Although adhesives having lower tack adhesion parameters mitigate some of the complications associated with protecting the tissue surrounding the anus, lowering the tack adhesion can exacerbate leakage and/or movement of the appliance during use. Such considerations can be particularly problematic for bedridden users as a majority of the weight of the user is born upon the hip area, and the appliance disposed between the user and the supporting surface, during rolling or shifting activities. Accordingly the contact interface of the appliance must be supple enough to accommodate cooperation with the contour of the anal cleft yet robust enough to maintain a desired engagement with user tissue surrounding the anus.

Another consideration associated with the use of such appliances is the ability of the appliance to adequately cooperate with the perineal area of the user. Inadequate cooperation of the appliance with the perineum can result in exposure of the urinary anatomy, such as the testes, penis, vagina, catheters or the like, to fecal matter. Exposure of such anatomy or medical appliances results in unsanitary conditions that tend to increase the incidence of bladder and/or urinary tract infections. Desired placement and maintained engagement of the area of the appliance that faces the forward positioned anatomy lessens the potential of such consequences but the close proximity and overlapping shape of the anatomy associated with the perineal area, particularly for prone users, complicates the ability to maintain a desired cooperation of the appliance with the user.

Still another consideration to the consideration of such appliances is in the construction of the container and the ability of the container to obtain a generally flat shape wherein opposite sides of the container overlay one another but are movable so as to not unduly interfere with the passage of fecal matter into the container. Some such appliances are so rigid and constructed such that portions of the appliance overlap the opening associated with the anus. The overlapping of the opening of the appliance with portions of the container tends to overstress the generally sealed interaction of the appliance with the anal area of the wearer resulting in leakage or displacement of the container relative to the anatomy of the wearer and can result in failure of the appliance to adequately capture the fecal matter in a sanitary manner.

Many such appliances also fail to provide an adequate methodology for providing a sealed configuration of fecal matter containing used appliances. Leaving an infirm user unattended for extended periods can result in the collection of an excessive volume of fecal matter rendering a closure methodology inoperable. Many such prior art appliances include supplemental containers associated configured to receive used appliances. Such methodologies increase the time and costs associated with servicing and maintaining such appliances.

Therefore, there is a need for anal fecal matter appliance that can be quickly and efficiently associated with the anus of a user; is constructed and cooperates with the user to provide a substantially circumferential interaction with the tissue of the user proximate the anus, including the perineal area; is not uncomfortable to use; and is constructed to cooperate with the anal cleft in a manner that does not interfere with passage of fecal matter into the appliance.

SUMMARY OF THE INVENTION

The present invention discloses a single use device for capturing fecal matter excreted from the anus of a user in a manner that resolves one or more of the shortcomings discussed above. One aspect of the present invention discloses a fecal matter containment appliance or device that maintains isolation of fecal matter from other anatomical features or structures including portions of the epidermis only slightly remote from the anal opening or anus as well as anatomy and medical devices, such as those associated with catheterization or otherwise related to urinary function, that may be positioned proximate the anus. The appliance mitigates contamination of adjacent anatomy and/or medical appliances from interaction with the excrement. The device includes a flexible fecal matter container having a closed end and an opening that is in fluid communication with a volume enclosed by the flexible container. An adhesive is disposed about the opening of the flexible container and has a first side that is secured to the flexible container. A second side of the adhesive is constructed to be removably applied to the epidermis of the user proximate an anal opening of the user. The adhesive is shaped to cooperate with the epidermis to circumscribe the anus in a sealed manner without interfering or overlapping anatomy associated with urinary function or medical devices, such as a catheter, associated therewith.

Another aspect of the invention discloses a fecal matter containment system having a flexible container that is constructed to receive fecal matter directly from an anus of a user and defined by a closed end and an opening formed through the container. An adhesive layer is attached to the flexible container and has a first side that is attached to the container and disposed circumferentially about the opening. A second side of the adhesive that is opposite the first side is selected to adhere to an epidermis of a user. The adhesive layer is shaped to define a passage that is aligned with the opening of the container and selectively securable to the epidermis of a user proximate the anal opening of a user.

Another aspect of the invention that is usable with one or more of the above aspects discloses a fecal matter containment appliance that includes a container formed of a flexible material. The container is disposable and defines a volume having a single inlet associated with an end of the container and a longitudinal length extending in a direction away from the end associated with the single inlet. The longitudinal length of the container is longer than any cross sectional dimension associated with the end associated with the single inlet. An adhesive layer is attached to the container and extends circumferentially about the inlet. The adhesive layer is defined by a first surface attached to the container about the inlet and a second surface opposite the first surface. The adhesive layer is deformable and compressible and the second surface has a tack adhesion that secures the container circumferentially about the anus of a user while removably cooperating with the tissue of the user.

Another aspect of the invention discloses a method of providing a fecal matter containment device. The method includes providing a flexible container having a closed end and an opening in fluid communication with an internal volume defined by the flexible container. An adhesive is provided that extends circumferentially about the opening and is safe for periodic application to and removal from an epidermis of a user. The adhesive is shaped to circumvent an anus of a wearer without interfering with anatomy associated with urine function of the wearer to maintain isolation between fecal matter and anatomy associated with the urine function.

These and other aspects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

In describing the various embodiments of the invention, which is illustrated in the drawings, specific terminology will be referred to for the sake of clarity. However, it is not intended that the invention be limited to the specific terms so selected and it is to be understood that each specific term includes all technical equivalents which operate in a similar manner to accomplish a similar purpose. For example, the words "connected", "attached", or terms similar thereto are often used. They are not limited to direct connection but include connection through other elements where such connection is recognized as being equivalent by those skilled in the art.

DETAILED DESCRIPTION OF THE PREFERRED EMBODIMENTS

The present invention and the various features and advantageous details thereof are explained more fully with reference to the non-limiting embodiments described in detail in the following description.

Figure 1:
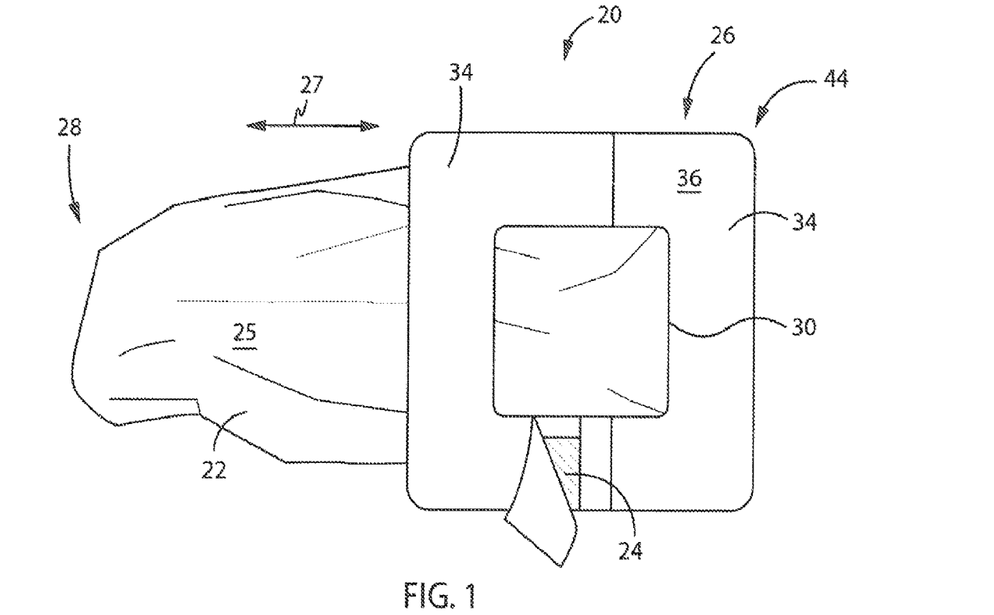
FIG. 1 is a perspective view of a fecal matter containment appliance according to one embodiment of the invention.
Figure 2:
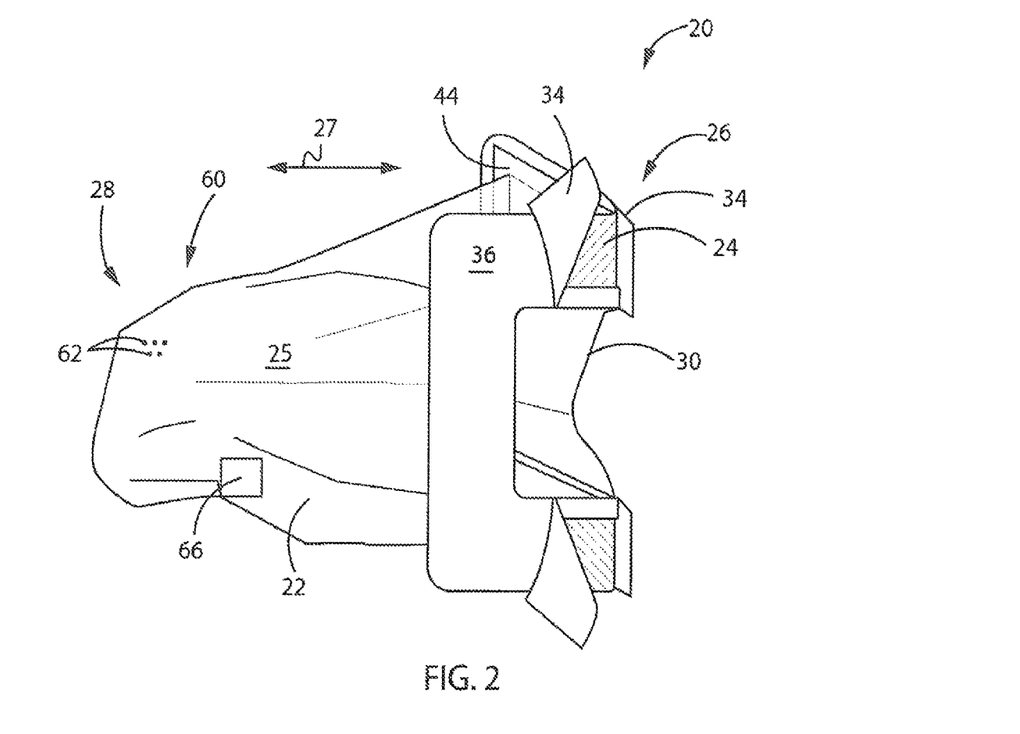
FIG. 2 is a view similar to FIG. 1 and shows an adhesive interface of the fecal matter containment appliance in a placement configuration wherein alternate sides of the adhesive surface generally overlie one another to facilitate placement of the appliance proximate an anus of a user.
Figure 3:
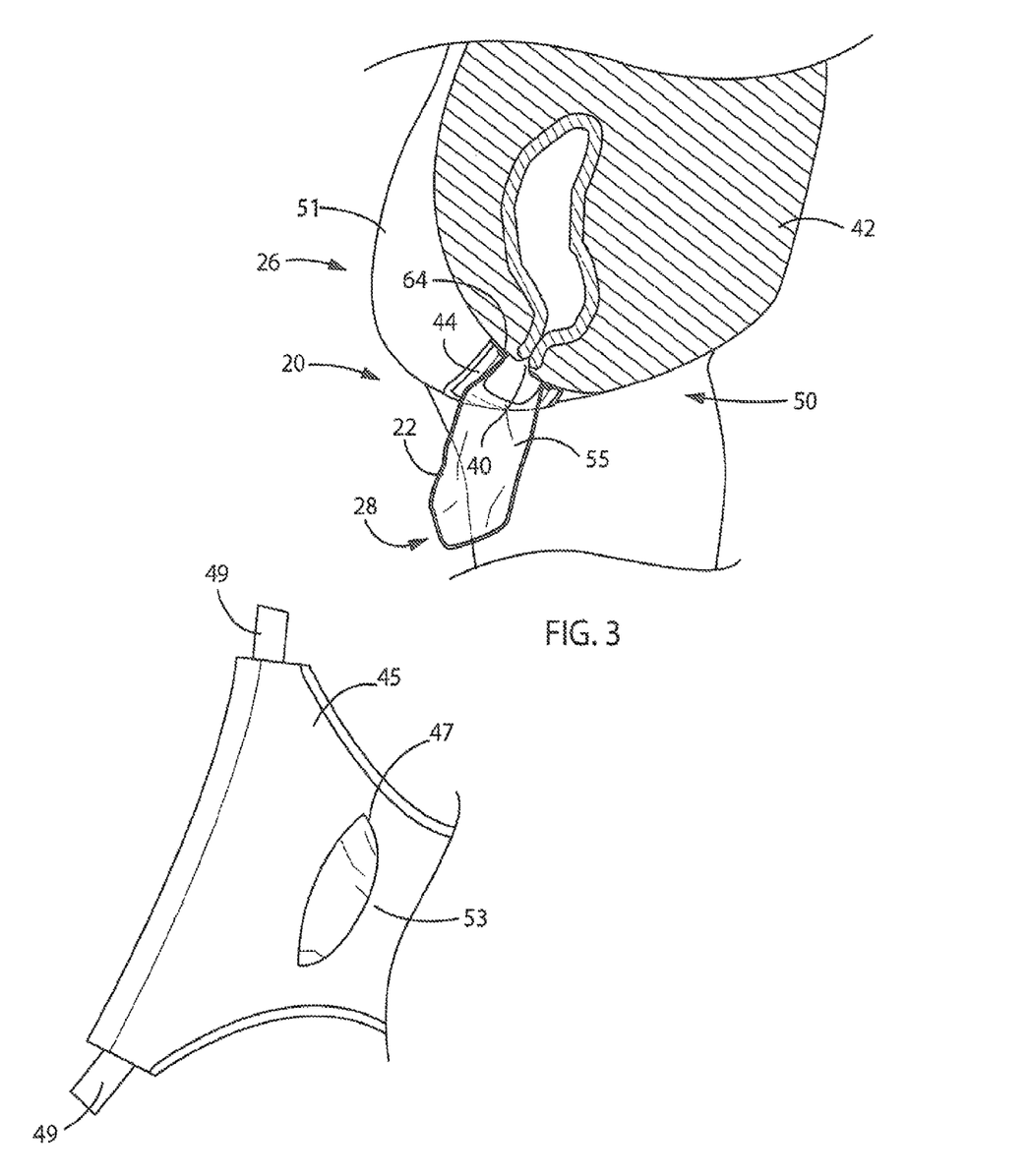
FIG. 3 is a partial cross-section view of the appliance associated with a user and includes an optional auxiliary urinary containment device configured to cooperate with the appliance shown in FIG. 1.
Figure 4:
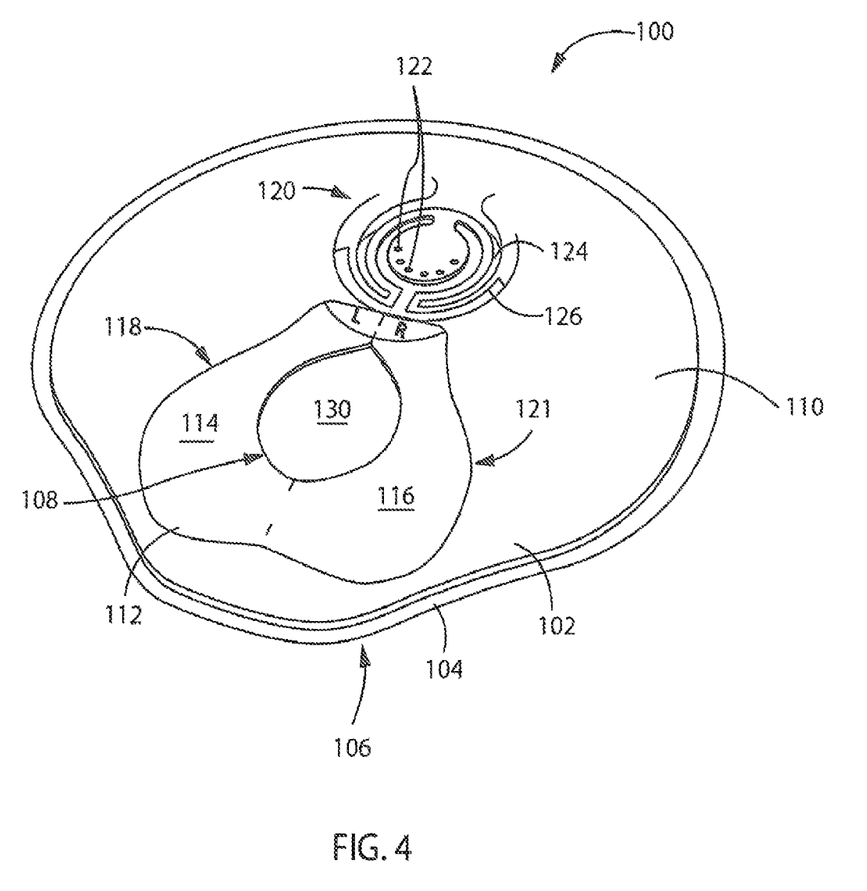
FIG. 4 is a perspective view of a fecal matter containment appliance according to another embodiment of the invention.
Figure 5:
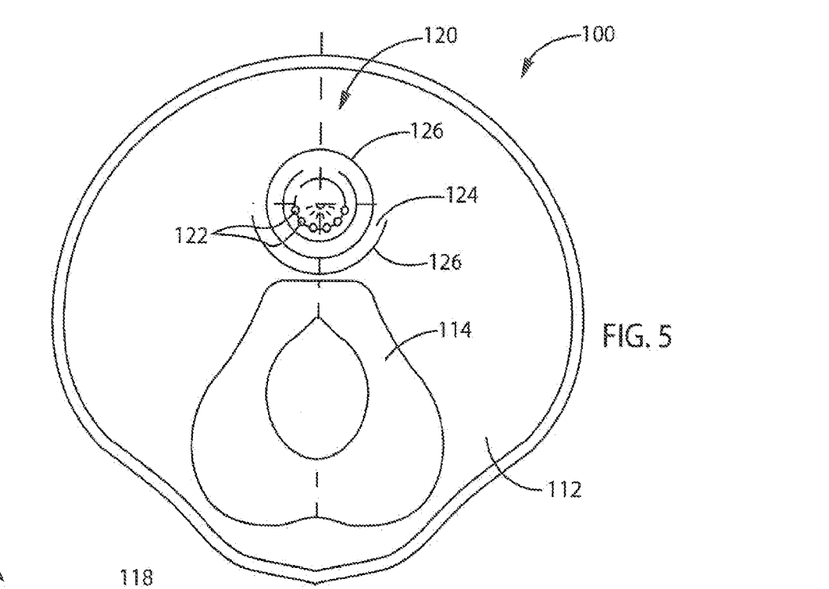
FIG. 5 is a plan view of a user facing side of the appliance shown in FIG. 4.

The present invention relates to a fecal matter containment appliance or device 20 that includes a disposable and flexible container 22 that is attached to a flexible adhesive 24 constructed to be removably secured to the epidermis of a user or wearer proximate the anal opening as is described further below. As shown in FIGS. 1-3, in a first embodiment, container 22 is defined by a body 25 that extends between an open end 26 and a closed end 28 such that container 22 generally defines a single blind opening. Body 25 includes a longitudinal length, indicted by arrow 27, that extends between ends 26, 28. Preferably, the value of length 27 is greater than a value associated with either dimension transversely oriented relative to length 27 associated with a cross section area of ends 26, 28. Container 22 and adhesive 24 of containment device 20 are preferably constructed of materials constructed to be to directly exposed to the epidermis of a wearer. It is appreciated that container 22 and adhesive 24 could be constructed of any number of suitable flexible materials such as plastic, rubber, woven or other materials. It is further appreciated that container 22 may be shaped to removably cooperate with auxiliary incontinence apparel or other apparel customarily exposed to the tissue of the wearer such as a washable cloth container or the like. Preferably, container 22 is constructed of a non-permeable material to facilitate expedient and sanitary disposal of soiled containment appliances or devices.

As disclosed further below, opening 30 is circumferentially bounded by adhesive 24 and shaped to generally circumscribe the anal opening of a wearer in generally close proximity thereto. Adhesive 24 extends circumferentially around opening 30 and is constructed to secure containment device 20 circumferentially to the epidermis of the user proximate the anal opening. One or more sections of a backing strip 34 are removably secured to a first or user side 36 of adhesive 24 to expose side 36 of adhesive 24 to atmosphere immediately prior to application of containment device 20. Adhesive 24 extends circumferentially about opening 30 to removably cooperate with the opposite lateral sides of the gluteus maximus or anal cleft, the coccyx superiorly, and the anus inferiorly or perineal structures such that opening 30 can be disposed in close proximity to the anal opening in a manner that prevents leakage of fecal matter from the cavity defined by container 22 to epidermis remote from the anal opening, urinary anatomic features or medical devices, and/or any clothing or garments associated therewith.

As shown in FIG. 3, containment device 20 is constructed to cooperate with a wearer or user 42 such that opening 30 of containment device 20 is aligned with the anal opening 40 of a user 42. Device 20 circumscribes the anal opening 40 and is adhered to the anatomy of user 42 by adhesive 24. Adhesive 24 includes side 36 (FIG. 2) or a first side that is constructed to removably cooperate with the epidermis of user 42 and a second side 44 that is non-removably connected to container 22. Although shown in a slightly expanded form, container 22 is preferably constructed of a pliable or deformable plastic material such that device 20 can be compactly and unobtrusively disposed beneath the garments or other clothing of user 42. Alternatively, device 20 may cooperate with an incontinence care product 45, or pocket 47 associated therewith, to mitigate contact between container 22 and the epidermis of user 42. As is commonly understood, product 45 and/or device 20 may include one or more straps or tabs 49 shaped to cooperate with the anatomy of user 42 so as to secure device 20 and/or product 45 relative thereto. Alternatively, container 22 may be formed to include a more comfortable and/or breathable material disposed along the exterior surface of the container to mitigate discomfort associated with direct contact of a plastic type material of container 22 with areas of the wearer that are offset from the anus. It is appreciated that when associated with device 20, tabs 49 can be configured to extend from container 22 and/or adhesive 24. It is further appreciated that such tabs 49 can be constructed to cooperate with other tabs and/or be configured to removably cooperate with the epidermis of the user via the inclusion of an adhesive. Device 20 cooperates with the user such that the anal area, and fecal matter associated therewith, can be hermitically separated from genitalia 50 or other medical accessories, such as catheters or the like, associated with urinary function.

Device 20 is constructed such that container 22 can be folded in various manners, such as folded in half, and adhered to the interior facing surfaces of the anal cleft 51. The flexible nature of device 20 allows the device to be discretely worn under clothing or other incontinence care products. As disclosed above, it is envisioned that a portion of container 22 can be passed through at least one layer 53 of a urinary incontinence product 45 so as to maintain isolation of the fecal matter container 22 from urinary waste. Both container 22 and adhesive 24 cooperate to define an opening that is large enough to allow fecal matter to pass therethrough and into the volume 55 associated with container 22 without detrimentally affecting the cooperation of adhesive 24 with either of container 22 and/or user 42. It is further envisioned that adhesive 24 could be formed integrally with container 22 to mitigate any separation therebetween. Preferably, length 27 of container 22 is suitable to allow tying of container 22 after use so as to capture any fecal matter contained therein. It is further envisioned that the patient facing side of adhesive 24 can be adhered to itself such that portions of container 22 overlap one another and effectively seal opening 30 when adhesive 24 is overlapped upon itself when discarded. Preferably, the tack adhesion associated with adhesive 24 is greater when introduced to itself than when associated with the epidermis of the user. Preferably, the tack adhesion of adhesive 24 is selected so as to provide a secure but removable interaction with the epidermis of the user in a manner that does not adversely affect the epidermis but is robust enough to accommodate flexure of the sphincter and incidental pulling forces attributable to interaction of container 22 during motion of the user and/or interaction of the container with support surfaces.

Referring briefly back to FIG. 2, device 20 preferably includes one or more vents 60 associated with expelling gaseous materials from container 22. In a simplest form, it is envisioned vent 60 can be formed by one or more very small openings, perforations or holes 62 formed through container 22. It is further appreciated that vent 60 may be disposed anywhere along the length or radial area associated with container 22. Preferably, vent 60 is disposed at a location least likely to be exposed to extended periods of waste products. Preferably, holes 62 are sized to tolerate only passage of gaseous materials through container 22 even when directly exposed to liquid or solid fecal matter. It is further appreciated that such functionality can also be provided via a gas permeable membrane or the like. Still referring to FIG. 2, device 20 may also include an optional odor control device, such as a charcoal filter 66 or the like associated with the volume 55 of container 22. Filter 66 mitigates the egress of odors associated with the fecal matter from device 20.

Length 27 of container 22 is preferably long enough to allow the user to place device 20 from a forward facing position. Length 27 of container is also preferably sufficient to allow a user or care provider to manually manipulate matter contained therein. Such considerations allow users with less limited infirmities to self place and service device 20 without excessive reaching and twisting common to usage of other appliances. The inner and outer radial dimensions associated with opening 64 and adhesive 24 are also preferably selected to accommodate a range of workable placement locations. When positioned for use, a longitudinally oriented portion of container 22 overlaps itself and is generally aligned with the direction of flow of excrement. Such a consideration allows container 22 to deflect in generally outward radially directions during introduction of the fecal matter to mitigate dispersal of the same in the outward radial directions toward the seal associated with adhesive 24.

It is appreciated that device 20 can be configured to be used by both male and female users or various ages including infants as well as other species, such as dogs, equines, and monkeys, wherein fecal matter containment is periodically desired. The circumferential cooperation of containment device 20 with the anatomy surrounding the anus, regardless of the species of user, reduces the potential for bladder infections or other deleterious effects associated with exposure to fecal matter. In human applications, containment device 20 can reduce incidence of emergency room visits, bed sores, and/or the application or consumption of antibiotics attributable to fecal matter contamination. The present invention is intended to overcome the deleterious effects attributable to the introduction of fecal matter into the urethra or other urinary anatomy. Device 20 also improves patient or user care via reduction of cleanup severity and duration as well as mitigates the necessity of the use of catheters to maintain the desired fecal and urinary waste isolation. Device 20 is further constructed to be readily usable by generally healthy users who may suffer from more intermittent periods of incontinence.

FIGS. 4-10 show a fecal matter containment appliance or device 100 according to another embodiment of the invention. Device 100 includes a container 102 generally defined by a perimeter edge 104 and having a closed end 106 and an opening 108 associated with an alternate or open end 110 of container 102. An adhesive layer 112 is disposed proximate and extends circumferentially about opening 108. One or more removable backer portions 114, 116 cooperate with a first or user facing side 118 of adhesive 112. A second side 121 opposite first side 118 of adhesive layer 112 is preferably permanently secured to container 102. Appliance 100 includes a vent 120 having one or more openings 122 associated with allowing egress of gases from container 102. Vent 120 can include a tortuous path 124 that is defined by a number of seam edges 126 associated with alternate layers of container 102. It is envisioned that seam edges 126 can be provided by alternate exterior surfaces of container 102 and/or be defined by a supplemental layer of material associated only with vent 120 disposed within a volume 130 defined by container 102. Tortuous path 124 mitigates the communication of solid and/or liquid matter to vent openings 122.

Figure 6:
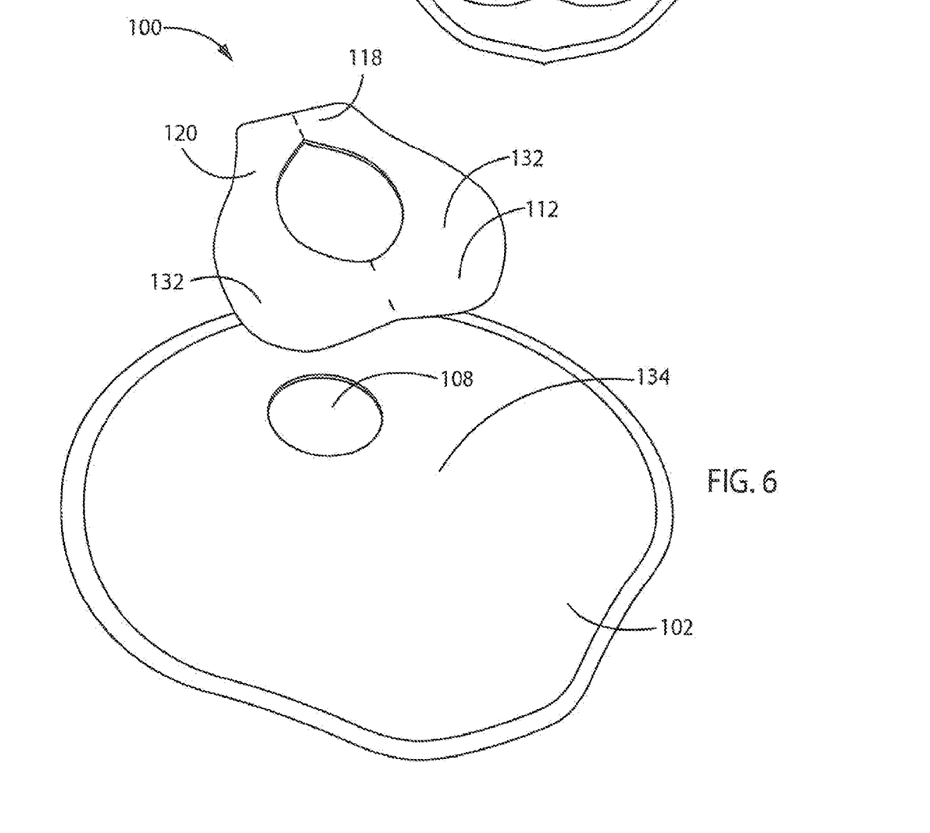
FIG. 6 is an exploded view of the appliance shown in FIG. 4 with the adhesive layer removed from the container.
Figure 7:
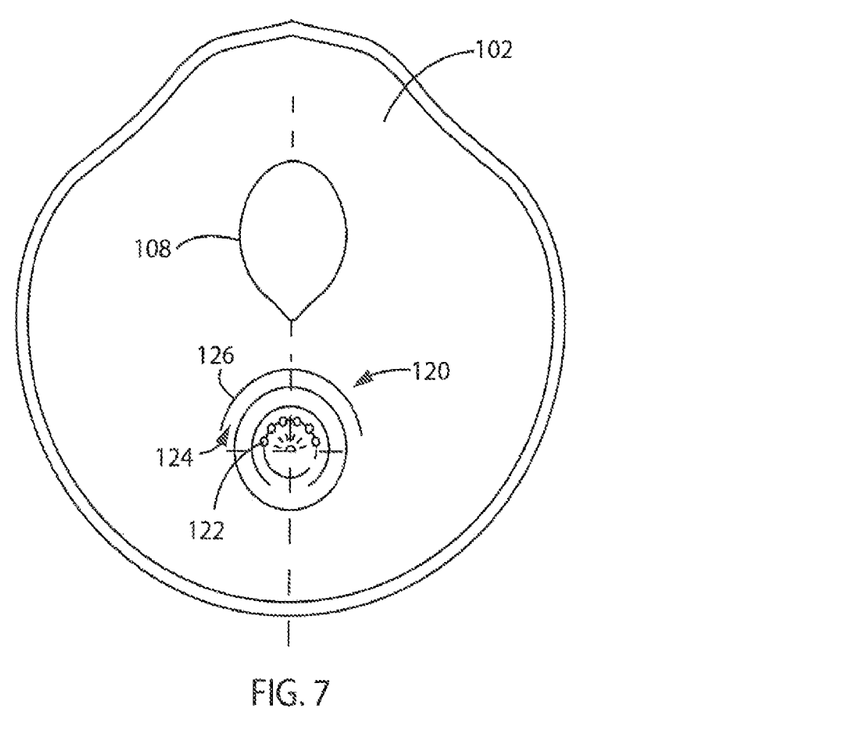
FIG. 7 is a plan view of the container of the appliance shown in FIG. 4.
Figure 8:
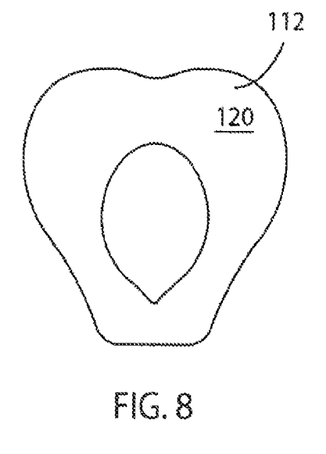
FIG. 8 is a plan view of an adhesive layer that can be associated with the opening of the container shown in FIGS. 1 and 4.

As shown in FIG. 6, first side 118 of adhesive layer 112 includes one or more pieces of a removable backing 132 that can be selectively removed from adhesive layer 112 during application of appliance 100. Second side 121 of adhesive layer 112 is shaped to cooperate with opening 108 of container 102 and be permanently affixed to a portion 134 of container 102 radially oriented proximate opening 108. It is appreciated that the size and shape of adhesive layer 112 can be manipulated to correspond with the size of opening 108 and provide a desired degree of tack adhesion with the epidermis of the user.

Figures 9, 10:
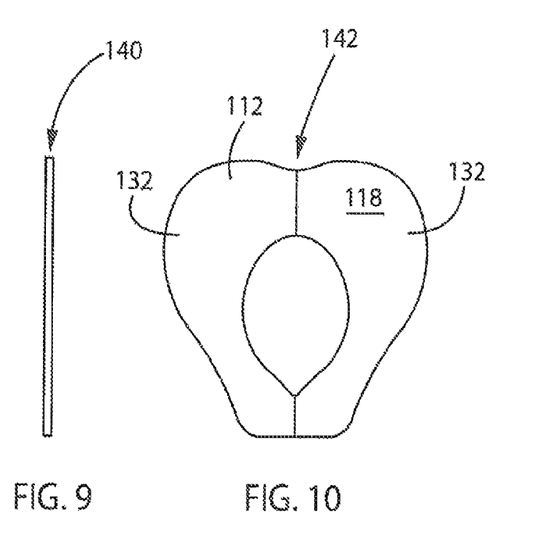
FIG. 9 is a side elevation view of the adhesive layer shown in FIG. 8.
FIG. 10 is similar to FIG. 8 and shows an alternate side of the adhesive layer shown therein.

Referring to FIGS. 9 and 10, adhesive layer 112 has a thickness 140 so as to not unduly interfere with the anatomy of the user when the buttocks are in close proximity to one another and a fold edge 142 to accommodate the desired placement of adhesive 112, and container 102 associated therewith, relative to the anatomy of the user. Referring back to FIG. 7, opening 108 and vent 120 are positioned relative to one another and relative to container 102 to provide offset orientations between opening 108 and vent 120 so as to further mitigate the egress of fecal matter from vent 120 during use of device 100. It is appreciated that opening 108 and vent 120 could be provided at alternate locations and or sides associated with container 102. Rather than or in addition to vent 120, it is further appreciated that appliance 100 may also include an odor absorbing structure or feature such as charcoal filter 66 to further improve the odor performance of appliance 100.

Figure 11:
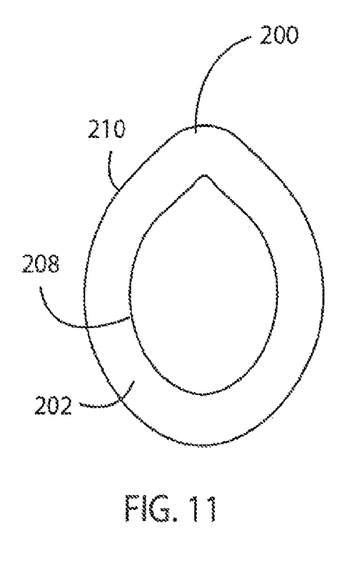
FIGS. 11-13 are views similar to FIGS. 8-10, respectively, of another adhesive layer usable with the container associated with the appliances shown in FIGS. 1 and 4.
Figures 12, 13:
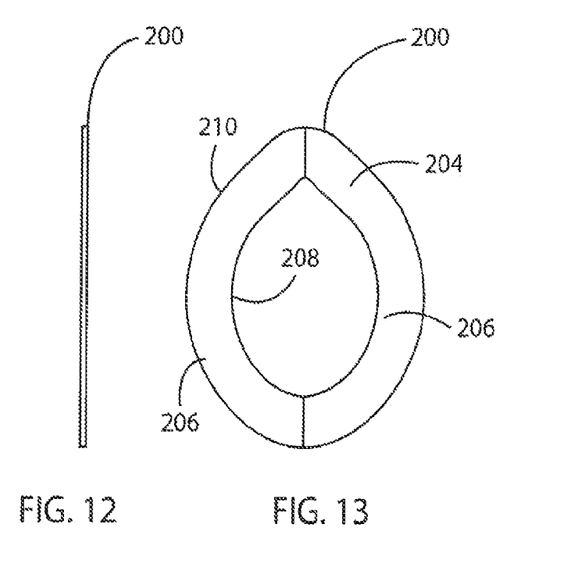
Figure 14:
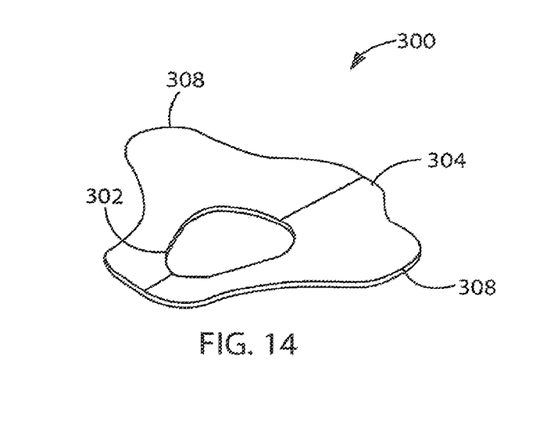
FIGS. 14-17 are various views of another adhesive layer that can associated with the container associated with the appliances shown in FIGS. 1 and 4.
Figure 15:
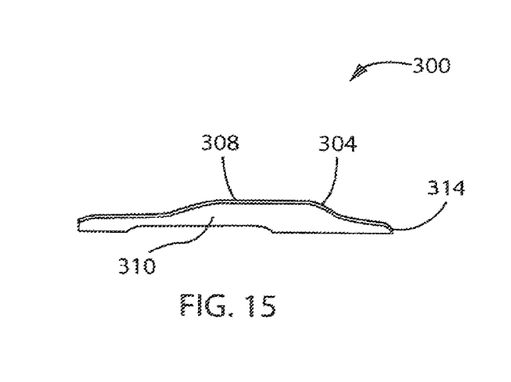
Figure 16:
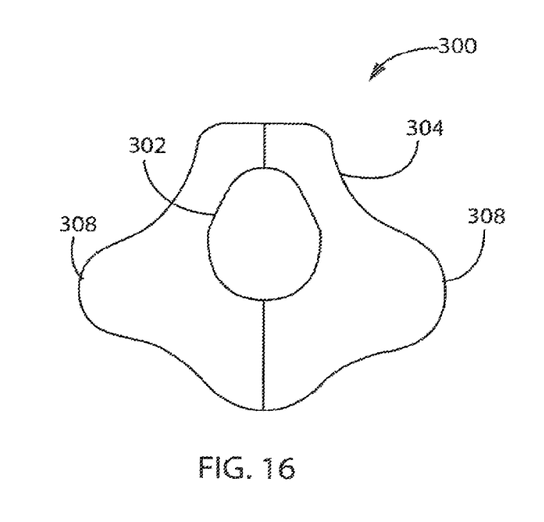

FIGS. 11-17 show various views of alternate embodiments associated with an adhesive layer usable with a pliable container of a respective fecal matter containment appliance. Referring to FIGS. 11-13, adhesive layer 200 includes a first side 202 constructed to be secured to container and the second side 204 having one or more removable backer strips 206 associated with accommodating selective exposure of the tack portion associated with the material of layer 200 disposed there behind. Adhesive layer 200 defines an opening 208 and a radially outer edge 210 shaped to cooperate with the opening of a respective container and is also constructed to not unduly interfere with the anatomy of the anal cleft of the user.

FIGS. 14-17 show an alternate embodiment of an adhesive layer 300 usable with a flexible container is disclosed above. Adhesive layer 300 includes an opening 302 that is shaped to generally correspond to an opening defined by the container and an outer radial edge 304 defined by adhesive layer 300. Rather than the generally circumferential configuration associated with adhesive layer 200, adhesive layer 300 includes one or more tabs 308 shaped to facilitate placement of adhesive layer 300 and the container associated therewith relative to the user and/or increase the task adhesion associated with the same. Tabs 308 extend is generally opposite outward radial directions relative to opening 302 and are preferably shaped to accommodate placement of the user's thumb or finger between a container facing surface 310 of adhesive layer 300 and the container associated therewith.

Figure 17:
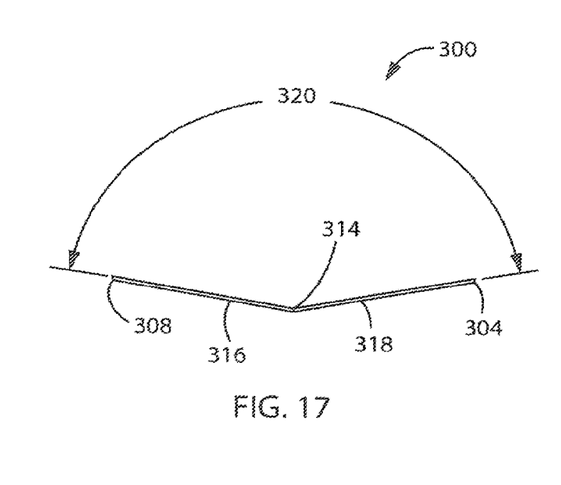

The portion of adhesive layer 300 associated with tabs 308 may include a tack surface and/or removable backer material associated with improving the adhesion between adhesive layer 300 and a respective container associated therewith. As shown in FIG. 17, adhesive layer 300 preferably includes a fold edge 314 associated with facilitating placement of adhesive layer 300 relative to the user. Preferably, adhesive layer 300 and fold edge 314 are configured to provide a stacking and/or presentation orientation of adhesive layer 300 and facilitate an intuitive presentation of the appliance relative to the anatomy of the user to facilitate alignment of the appliance with the perineum and the anus. Alternate lateral sides 316, 318 of adhesive layer 300 are oriented at an angle relative to one another, indicated by arrow 320, to provide an intuitive indication as to the orientation of adhesive layer 300 and alignment of the same with the anal cleft of the user. Such a configuration also improves stacking performance of multiple appliances by providing an indexing arrangement of one appliance relative to an adjacent appliance.

Figure 18:
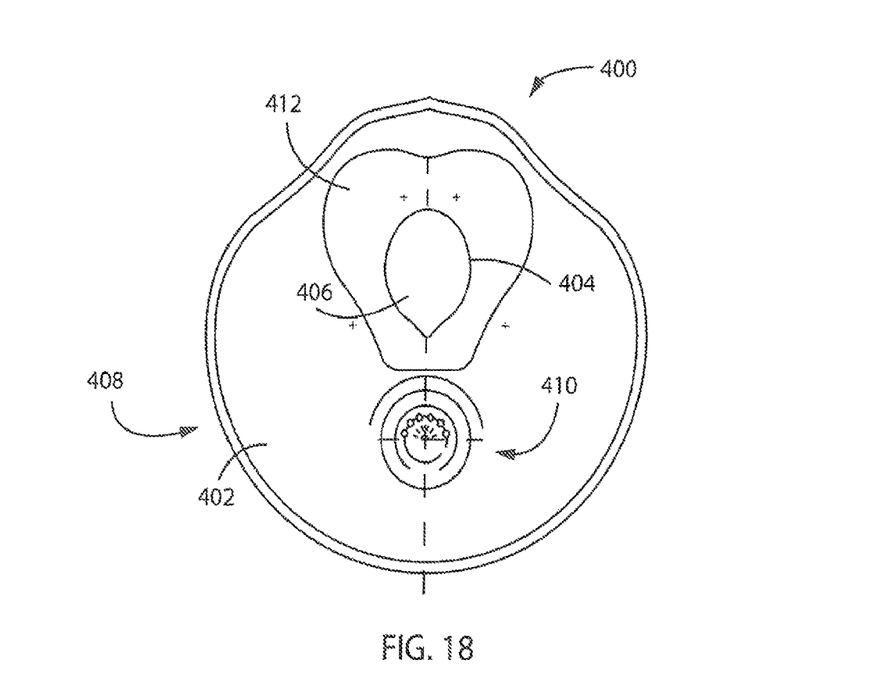
FIG. 18 is a plan view of a fecal matter containing appliance according to another embodiment of the invention.
Figure 19:
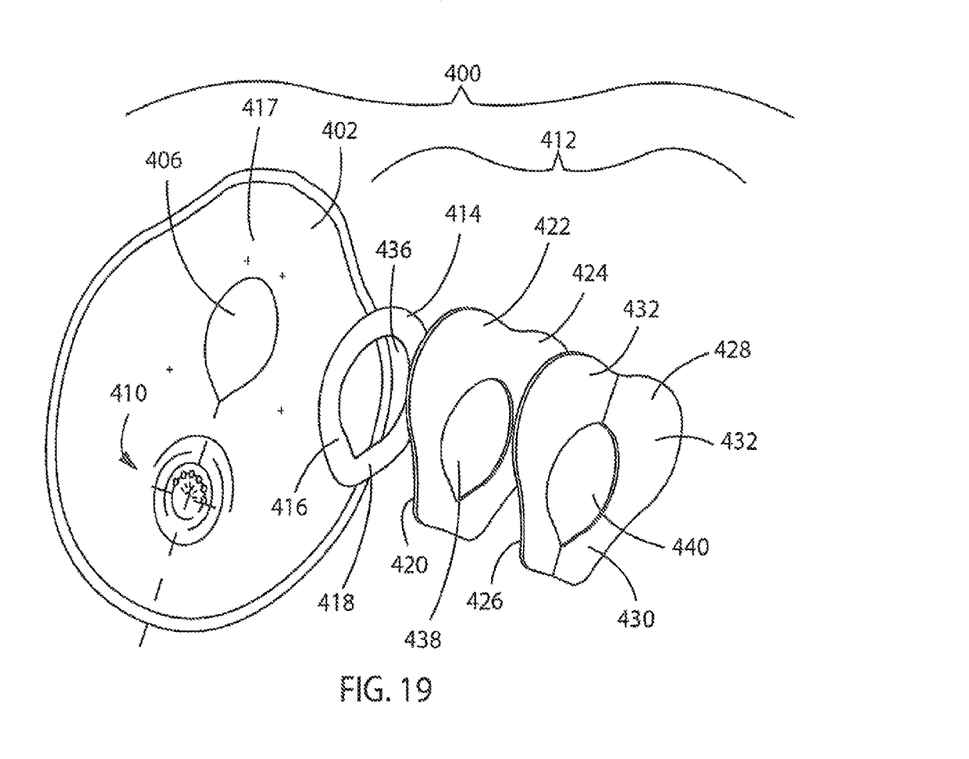
FIG. 19 is an exploded view of the appliance shown in FIG. 18.

FIGS. 18 and 19 show another embodiment of a fecal matter containment appliance or device 400 according to the present invention. Device 400 includes a flexible or pliable container 402 having an open end 404 with an opening 406 formed thereat and a closed end 408 that is disposed generally opposite open end 404. Device 400 includes an optional vent 410 like that disclosed above that is offset from opening 406 formed in container 402. It is further appreciated that vent 410 may be formed as a plurality of passages, may include a gas permeable member, and/or may include a valve flap internal to the appliance which directs solid or liquid waste products away from the respective passage(s) associated with the vent.

Device 400 includes a multi-ply adhesive layer 412 that is shaped to cooperate with opening 406 of container 402. The first ply 414 of adhesive layer 412 includes a first surface 416 shaped a sealingly cooperate with a portion 417 of container 402 oriented radially about opening 406. A second surface 418 of ply 414 sealingly cooperates with a first surface 420 of a compressible ply 422 of adhesive layer 412. Preferably, compressible ply 422 maybe formed of a foam type material. A second surface 424 of ply 422 sealingly cooperates with a first surface 426 of a second adhesive ply 428 associated with adhesive layer 412.

A patient facing surface 430 of ply 428 includes one or more removable backing layers 432 shaped a removably cooperate with surface 430 so as to expose the tack adhesive disposed there behind. Each ply 414, 422, 428 includes a respective opening 436, 438, 440 that is shaped to generally overlie and circumscribe opening 406 associated with container 402. The cooperation of ply 414 with ply 422 allows a portion of ply 422 and ply 428 to remain unsecured from container 402 to accommodate passage of the finger or thumb of a user between adhesive layer 412 and container 402 to enhance placement of device 400. It is further appreciated that one or more of plys 414, 422, 428 and/or backing layers 432 may include a grab such as a pull tab or similar such extension of the respective ply or backing layer to better facilitate interaction of the user with the respective adhesive layer. Such grabs or tabs generally cooperate with the respective adhesive layer to attain a desired presentation of the adhesive layer, and selective exposure of the tack adhesive, during placement and/or removal of the appliance and facilitate movement or deformation of the container to achieve a desired orientation and placement of the appliance.

It is further appreciated that surface 420 of ply 422 may also include a removable backing and be provided with a tack portion for securing the entire footprint of ply 422 and ply 428 to respective portions of container 402 proximate opening 406 after placement of device 400 relative to the user. Such a consideration mitigates folding and/or overlapping orientations of adhesive layer 412 during use of device 400. Is it further envisioned that one or more of plys 414, 422, 428 be provided with a physical memory and or contour so as to facilitate an intuitive and indexing presentation of adhesive layer 412 and/or the entirety of the device 400 associated therewith relative to the anatomy associated with the anal cleft of the user as disclosed above.

Preferably, the shape and size of the adhesive layer and the container associated with the various appliances disclosed herein are configured to provide proximate placement of the appliance relative to the anus of the user in a manner wherein the adhesive layer fully engages the perineal area of the user as well as circumscribing portions of the buttocks such that the appliance circumscribes the anus, can accommodate flexure of the sphincter during defecation, and orients the container such that the closed end is generally offset in the longitudinal direction relative to the open end associated with a respective adhesive layer. Such considerations accommodate substantially outward radial expansion of the respective container during the introduction of fecal thereby mitigating the detrimental consequences associated with fecal matter back pressure in a direction toward the interior radial edge associated with the adhesive layer and the cooperation of the same with the anatomy of the user so as to maintain a desired sealed interaction between the adhesive layer and the anatomy of the user. Such considerations also limit tension and/or compression forces associated with the seal between the adhesive layer and the respective container until manual removal of the appliance is desired. It is further appreciated that any or all of the respective adhesive layers disclosed above could alternatively be formed integrally with the respective container so as to negate any separable interaction between the container and the respective adhesive layer short of structural failure of the container. The present invention discloses fecal matter containment appliances that can be conveniently removably secured proximate the anus of the user and perform in a manner wherein undesired exposure of the user to feces can be mitigated if not wholly eliminated. The various appliances also mitigate the detrimental consequences associated with exposure of the urinary features and/or medical appliances associated therewith to fecal matter.

Therefore, one embodiment of the invention includes a fecal matter containment system having a flexible container that is constructed to receive fecal matter directly from an anus of a user and is defined by a closed end and an opening formed through the container. An adhesive layer is attached to the flexible container and has a first side that is attached to the container and disposed circumferentially about the opening. A second side of the adhesive that is opposite the first side is selected to adhere to an epidermis of a user. The adhesive layer is shaped to define a passage that is aligned with the opening of the container and selectively securable to the epidermis of a user proximate the anal opening of a user.

Another aspect of the invention that is usable with one or more of the above aspects discloses a fecal matter containment appliance that includes a container formed of a flexible material. The container is disposable and defines a volume having a single inlet associated with an end of the container and a longitudinal length extending in a direction away from the end associated with the single inlet. The longitudinal length of the container is longer than any cross sectional dimension associated with the end associated with the single inlet. An adhesive layer is attached to the container and extends circumferentially about the inlet. The adhesive layer is defined by a first surface attached to the container about the inlet and a second surface opposite the first surface. The adhesive layer is deformable and compressible and the second surface has a tack adhesion that secures the container circumferentially about the anus of a user while removably cooperating with the tissue of the user.

Another embodiment of the invention includes a method of providing a fecal matter containment device. The method includes providing a flexible container having a closed end and an opening in fluid communication with an internal volume defined by the flexible container. An adhesive is provided that extends circumferentially about the opening and is safe for periodic application to, and removal from, an epidermis of a user. The adhesive is shaped to circumvent an anus of a wearer without interfering with anatomy associated with urine function of the wearer to maintain isolation between fecal matter and anatomy associated with the urine function.

It is appreciated that the various fecal matter containment appliance assemblies disclosed herein include various additions, modifications, and rearrangements that are within capabilities of those skilled in the art from the disclosure of the present application. It is intended that the appended claims cover all such additions, modifications, and rearrangements. Expedient embodiments of the present invention are differentiated by the appended claims which also form part of the specification.

What is claimed is:

1. A fecal matter containment system comprising:
a flexible container constructed to receive fecal matter directly from an anus of a user and defined by a closed end and an opening formed through the container;
an adhesive layer having a first side that is attached to the container and disposed circumferentially about the opening and a second side opposite the first side and selected to adhere to an epidermis of a user, wherein the adhesive layer is shaped to define a passage that is aligned with the opening of the container and selectively securable to the epidermis of a user proximate an anal opening of a user;
at least one of a vent formed in the flexible container; and,
tortuous path proximate the vent defined by a plurality of seams that are radially offset from the vent and are formed by the flexible container.

2. The fecal matter containment system of claim 1 wherein the adhesive layer has a shape that is securable to the epidermis of a user circumferentially about the anal opening of the user without interfering with urinary anatomy of a user.

3. The fecal matter containment system of claim 1 wherein the container has a length that extends between the closed end and the opening that is sufficient to allow knotting of a container having fecal matter disposed in a volume of the container.

4. The fecal matter containment system of claim 1 further comprising an absorbent undergarment constructed to surround the flexible container.

5. The fecal matter containment system of claim 4 wherein the absorbent undergarment includes a first layer that is exposed to the epidermis of a user and a second layer that is exposed to atmosphere.

6. The fecal matter containment system of claim 5 wherein the container is at least one of exposed to the first layer and isolated from the second layer of the absorbent undergarment and disposed between the first and second layers.

7. The fecal matter containment system of claim 1 further comprising an odor absorbent insert contained in the container and at a location offset from the opening.

8. The fecal matter containment system of claim 1 wherein the adhesive layer is contoured to provide a three-dimensional non-planar presentation of the adhesive layer that is an indicia of placement of the flexible container relative to an anal cleft of a user.

9. The fecal matter containment system of claim 1 further comprising at least one grab site formed proximate an outer radial edge of the adhesive layer proximate the opening such that a finger or thumb of a user can be positioned between the adhesive layer and the flexible container during placement of the opening proximate the anus.

10. The fecal matter containment system of claim 1 further comprising at least one of a strap and a tab extending in an outward radial direction beyond the flexible container.

11. A fecal matter containment appliance comprising:
a container formed of a flexible material, the container being disposable and defining a volume having a single inlet associated with an end of the container and a longitudinal length extending in a direction away from the end wherein the longitudinal length is longer than any cross sectional dimension associated with the end;
an adhesive layer attached to the container and extending circumferentially about the inlet, the adhesive layer defined by a first surface attached to the container about the inlet and a second surface opposite the first surface, the adhesive layer being deformable and compressible and the second surface having a tack adhesion that secures the container circumferentially about an anus of a user while removably cooperating with epidermis tissue of the user;
a gap formed between a portion of an outward radial edge of the adhesive layer and the container wherein the gap extends toward the opening a distance sufficient to allow placement of a user thumb or finger between the adhesive layer and the container to facilitate placement of the fecal matter containment appliance relative to the anus;
a backer that removably cooperates with the second surface of the adhesive layer to expose the second surface when the backer is removed therefrom;
a vent that is defined by at least one hole formed through the container at a location offset from the inlet; and at least one of a valve and tortuous path proximate the vent and wherein at least one of the vent and at least one of the valve and tortuous path configured to prevent egress of fecal matter from the container via the vent.

12. The fecal matter containment appliance of claim 11 further comprising a disposable odor arrestor disposed in the container.

13. A method of providing a fecal matter containment device, the method comprising:
   providing a flexible container having a closed end and an opening in fluid communication with an internal volume defined by the flexible container;
   providing an adhesive that is safe for periodic application to and removal from an epidermis of a user;
   shaping the adhesive to circumvent an anus of a wearer without interfering with anatomy associated with urine function of the wearer to maintain isolation between fecal matter and anatomy associated with the urine function;
   providing at least one vent formed through the flexible container at a location offset from the opening; and
   forming a tortuous path proximate the vent that is defined by a plurality of seams that are radially offset from the vent and are formed by the flexible container.

14. The method of claim 13 further comprising providing an absorbent garment that is shaped to be worn by a wearer and overlap the flexible container.

15. The method of claim 14 further comprising providing a passage that extends at least partly through the absorbent garment and is shaped to accommodate passage of the flexible container therethough such that a portion of the flexible container remote from the opening is disposed between adjacent layers of the absorbent garment.

16. The method of claim 13 further comprising providing at least one of:
   at least one removable non-adhesive strap secured to at least one of the flexible container and the adhesive, and at least one adhesive tab that extends in an outward radial direction from the adhesive that removably cooperates with the epidermis of a user for augmenting securing the fecal matter containment device relative to the wearer.

* * * * *

UNITED STATES PATENT AND TRADEMARK OFFICE
CERTIFICATE OF CORRECTION

PATENT NO. : 10,076,439 B2
APPLICATION NO. : 14/897000
DATED : September 18, 2018
INVENTOR(S) : James K. Paley It is certified that error appears in the above-identified patent and that said Letters Patent is hereby corrected as shown below:

In the Specification

Column 2, Line 10 Remove "," after can

In the Claims

Claim 1, Column 11, Line 65 Add --a-- before tortuous

Signed and Sealed this
Eighth Day of January, 2019

Andrei Iancu
*Director of the United States Patent and Trademark Office*